United States Patent [19]

Skotnicki et al.

[11] Patent Number: 5,252,579
[45] Date of Patent: Oct. 12, 1993

[54] MACROCYCLIC IMMUNOMODULATORS

[75] Inventors: Jerauld S. Skotnicki, Allentown; Amedeo A. Failli, Princeton Junction; Robert J. Steffan, Langhorne; Robert M. Kearney, Lawrenceville, all of N.J.

[73] Assignee: American Home Products Corporation, New York, N.Y.

[21] Appl. No.: 17,586

[22] Filed: Feb. 16, 1993

[51] Int. Cl.$^5$ .................. C07D 491/16; A61K 31/345
[52] U.S. Cl. ..................................... 514/291; 540/456
[58] Field of Search .......................... 540/456; 514/291

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 540/456 |
| 4,401,653 | 8/1983 | Eng | 540/456 |
| 4,650,803 | 3/1987 | Stella et al. | 540/456 |
| 4,885,171 | 12/1989 | Sehgal et al. | 540/456 |
| 5,078,999 | 1/1992 | Warner et al. | 540/456 |
| 5,080,899 | 1/1992 | Sturm et al. | 540/456 |
| 5,091,389 | 2/1992 | Ondeyka et al. | 540/456 |
| 5,100,883 | 3/1992 | Schiehser | 540/456 |
| 5,100,899 | 3/1992 | Calne | 540/456 |
| 5,102,876 | 4/1992 | Caufield | 540/456 |
| 5,118,677 | 6/1992 | Caufield | 540/456 |
| 5,118,678 | 6/1992 | Kao et al. | 540/456 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |

FOREIGN PATENT DOCUMENTS

| | | | |
|---|---|---|---|
| 507555A1 | 7/1992 | European Pat. Off. | 540/456 |
| 525960A1 | 2/1993 | European Pat. Off. | 540/456 |

OTHER PUBLICATIONS

Luengo et al., "Tetrahedron Letters", vol. 34, pp. 991–994 (1993).
Yohannes et al., Tetrahedron Letters vol. 33 pp. 7469–7472 (1992).
Vezina, C., J. Antibiot. 28: 721 (1975).
Sehgal, S. N., J. Antibiot. 28: 727 (1975).
Baker, H. J., Antibiot. 31:539 (1978).
Martel, R. R., Can. J. Physiol. Pharmacol. 55:48 (1977).
Staruch, M. J., FASEB 3: 3411 (1989).
Dumont, F. J., FASEB 3: 5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Gregory et al., J. Heart Lung Transplant. 11 (pt. 2): 197 (1992).
Meiser et al., J. Heart Lung Transplant 9: 55 (1990).
Stepkowski, S. M., Transplantation Proc. 23: 507 (1991).

*Primary Examiner*—Robert T. Bond
*Attorney, Agent, or Firm*—Arnold S. Milowsky

[57] ABSTRACT

This invention provides a compound of the structure

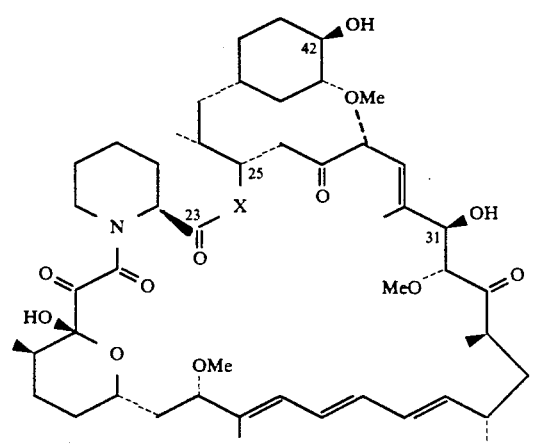

wherein
X is selected from the group consisting of —NR$^1$CR$^2$R$^3$(CR$^4$R$^5$)$_m$S—, —NR$^1$CR$^2$R$^3$(CR$^4$R$^5$)$_m$O—, —OCR$^2$R$^3$(CR$^4$R$^5$)$_m$O—, —NR$^1$CR$^2$R$^3$(CR$^4$R$^5$)$_p$—, —OCR$^2$R$^3$(CR$^4$R$^5$)$_p$—, —NR$^1$CR$^2$R$^3$(CR$^4$R$^5$)$_m$NR$^6$—, —OCR$^2$R$^3$(CR$^4$R$^5$)$_m$NR$^6$—, —SCR$^2$R$^3$(CR$^4$R$^5$)$_m$NR$^6$—, —SCR$^2$R$^3$(CR$^4$R$^5$)$_m$S—, —NOR$^1$—, and —NR$^1$—;
R$^1$, R$^2$, R$^3$, R$^4$, R$^5$, and R$^6$ are each, independently, hydrogen, alkyl, fluorine, trifluoromethyl, aryl, arylalkyl, or any pair taken together to form a 3–6 membered ring;
m = 1–6; and
p = 0–6 or a pharmaceutically acceptable salt thereof which is useful as an immunosuppressive, antiinflamatory, antifungal, antiproliferative, and antitumor agent. This invention also covers derivatives of I and the use of I in combination with other immunoregulatory agents.

13 Claims, No Drawings

MACROCYCLIC IMMUNOMODULATORS

BACKGROUND OF THE INVENTION

This invention provides macrocyclic immunomodulators related to rapamycin and a method for using them for inducing immunosuppression, and in the treatment of transplantation rejection, host vs. graft disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al, J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in RASEB 3, 3411 (1989) and its utility in preventing transplantation rejection shown in U.S. Pat. No. 5,100,899. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al, Lancet (1978)].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990) and European Patent Application 507,555 A2], and smooth muscle cell proliferation and intimal thickening following vascular injury [Morris, R. J. Heart Lung Transplant 11 (pt. 2); 197 (1992)].

Mono- and diacylated derivatives of rapamycin (esterified at the 28, and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

The degradation of rapamycin with lead tetraacetate or sodium cyanoborohydride/benzyl amine into synthons for total synthesis has been reported [Yohannes, D., Tet. Letters 33:7469 (1992)].

DESCRIPTION OF THE INVENTION

This invention provides derivatives of rapamycin which are useful as immunosuppressive, antiinflammatory, antifungal, antiproliferative, and antitumor agents having the structure

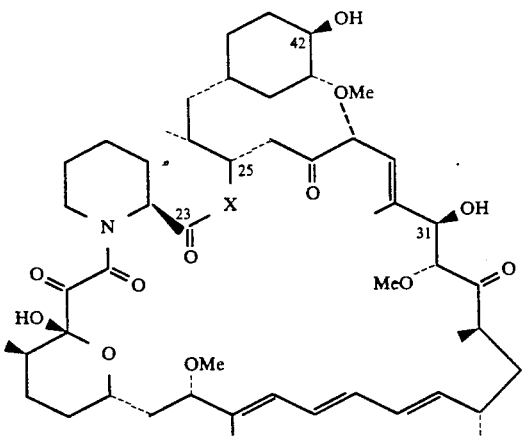

wherein
X is selected from the group consisting of
$-NR^1CR^2R^3(CR^4R^5)_mS-$,
$-NR^1CR^2R^3(CR^4R^5)_mO-$, $-OCR^2R^3(CR^4R^5)_mO-$, $-NR^1CR^2R^3(CR^4R^5)_p-$,
$-OCR^2R^3(CR^4R^5)_p-$, $-NR^1CR^2R^3(CR^4R^5)_mNR^6-$,
$-OCR^2R^3(CR^4R^5)_mNR^6-$,
$-SCR^2R^3(CR^4R^5)_mNR^6-$, $-SCR^2R^3(CR^4R^5)_mS-$, $-NOR^1-$, and $-NR^1-$;

$R^1$, $R^2$, $R^3$, $R^4$, $R^5$, and $R^6$ are each, independently, hydrogen, alkyl of 1-6 carbon atoms, fluorine, trifluoromethyl, aryl, arylalkyl or 7-10 carbon atoms, or may pair taken together to form a 3-6 membered ring;

m=1-6; and p=0-6 or a pharmaceutically acceptable salt thereof.

Of these compounds, preferred members are those in which X is $-NR^1CR^2R^3(CR^4R^5)_mS-$ and those in which X is $-NR^1CR^2R^3(CR^4R^5)_mS-$ and $R^1$, $R^2$, $R^3$, $R^4$, and $R^5$ are each, independently, hydrogen or alkyl of 1-6 carbon atoms. It is preferred that the aryl portion of the arylalkyl substituent is a phenyl, naphthyl, pyridyl, quinolyl, isoquinolyl, quinoxalyl, thienyl, thionaphthyl, furyl, benzofuryl, benzodioxyl, benzoxazolyl, or benzodioxolyl group that may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, $-SO_3H$, $-PO_3H$, and $-CO_2H$. It is more preferred that the aryl moiety is a phenyl group that is optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthiol of 1-6 carbon atoms, $-SO_3H$, $-PO_3H$, and $-CO_2H$.

Pharmaceutically acceptable salts may be formed from organic and inorganic acids and bases. These salts may be typically formed when X contains a basic amino group or when an arylalkyl substituent contains a basic or acidic moiety. Preferred organic and inorganic acids are those such as acetic, lactic, citric, tartaric, succinic, maleic, malonic, gluconic, hydrochloric, hydrobromic, phosphoric, nitric, sulfuric, methanesulfonic, and the like. Preferred organic and inorganic salts are those such as sodium, potassium, tromethamine, trialkylamine, benzylamine, and the like. Based on this disclosure, other pharmaceutically acceptable salts that can be formed will be readily apparent to one skilled in the art.

ine, imidazole, and ammonium hydroxide, will also facilitate the ring opening reaction shown below.

Scheme 1

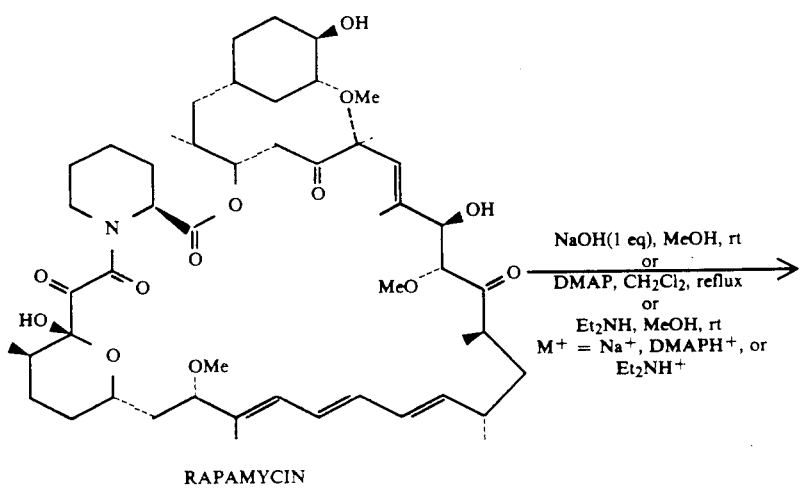

RAPAMYCIN

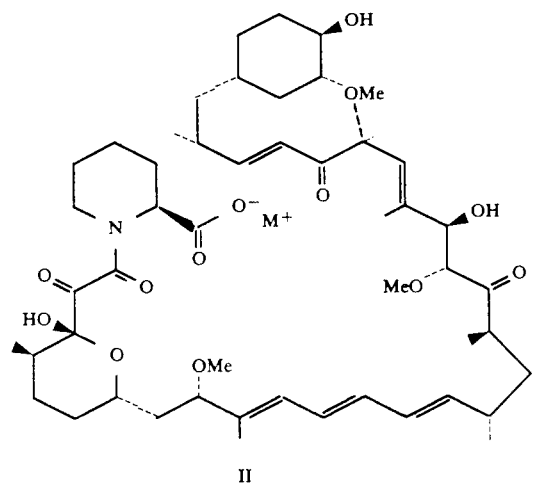

II

This invention also covers the use of the compounds of this invention administered in conjunction with one or more other immunoregulatory agents for use in inducing immunosuppression or as an antiinflamatory agent. Such other immunoregulatory agents include, but are not limited to azathioprine, corticosteroids, such as prednisone and methylprednisone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention can be prepared by initially ring opening rapamycin at the 24,25-bond under basic conditions as illustrated in Scheme I below. Other nitrogenous bases, such as pyridine, triethylamine, benzylamine, and the like.

Intermediate II can be converted to 25,26-dehydro-24,25-secorapamycin (secorapamycin, III) by acidification of intermediate II with a dilute acid, such as dilute acetic acid, during the work up, or by subjecting intermediate II directly to chromatography. The structure of secorapamycin is shown below.

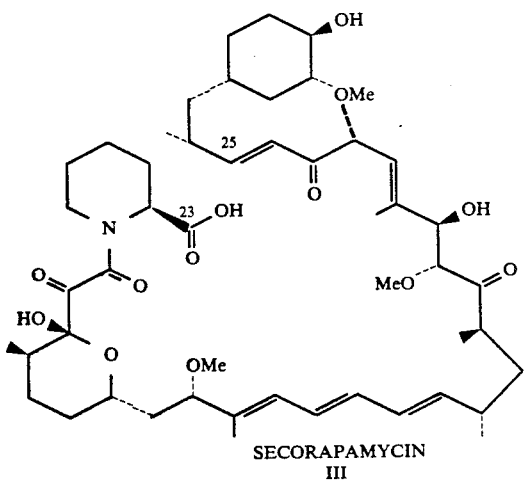

SECORAPAMYCIN
III

Care must be taken during the workup of intermediate II, as overacidification of II resulted in the formation of a 2-hydroxy-3,5-diketomorpholine isomeric secorapamycin (IV) and a spirolactone corresponding to dehydrated secorapamycin (V). The compound of formula IV is named 23,25-deepoxy-15-dioxo-25,26-didehydro-15,23-epoxyrapamycin, and the compound of formula V is named 7-{[6S-[22-(4R-hydroxy-3R-methoxy-1S-cyclohexyl)-14R-hydroxy-2S,13R-dimethoxy-3,9S,11R,15,17R,21R-hexamethyl-12,18-dioxodocosa-3E,5E,15E,19R-pentaenyl]-4R-methyl-spiro[oxapane-2,3'-tetrahydropyrido[2,1-c] [1,4]oxazine-1',3',4'-trione. Compound V can also be formed directly from secorapamycin by treatment with a mixture of 1-(3-dimethylaminopropyl)-3-ethyl carbodiimide (DAEC), hydroxybenzotriazole (HOBT), and N-methylmorpholine. The formation of these compounds are shown below in Scheme 2.

center first adds via a Michael type addition to the 25-position of secorapamycin, followed by nucleophilic reaction with the 23-carbonyl and subsequent loss of water to provide the compounds of this invention. In general, the Michael addition reaction can be accomplished under standard reaction conditions that are well described in the literature. More specifically, the Michael reaction for sulfur containing nucleophiles can be accomplished under mildly basic conditions, such as triethylamine or dimethylaminopyridine. The Michael addition for oxygen containing nucleophiles can be accomplished by generating an oxygen anion, with a base such as sodium hydride. The Michael addition for nitrogen containing nucleophiles can be accomplished either using a base such as triethylamine, or by using a copper catalyst such as cuprous chloride. The Michael addition for carbon nucleophiles can be accomplished via the cuprate or under other standard 1,4-Michael addition conditions. Following the Michael addition, the second nucleophilic addition and dehydration can be facilitated by using a coupling reagent such as 1-(3-dimethylaminopropyl)-3-ethyl carbodiimide (DAEC). Compounds in which X is —NR¹— or —NOR¹— are made using the methodology described above. When an alcohol is to be added as the second nucleophile, it is necessary that the alcohol be protected with a suitable alcohol protecting group, such as a silyl ether, a THP ether, a benzyl ether, or the like during the initial Michael addition, followed by removal of the protecting group, and coupling as described above. Similarly, where an amine is to be added as the second nucleophile, protection of this amine prior to the Michael addition with a suitable protecting group, such as benzyl, trityl, CBZ, or FMOC, allows regiochemical control of the two reactions. This protection of the amine, however, is not necessary when sulfur is the nucleophile added via the Michael addition. Additionally, the amine may be a masked amine, such as a nitro group, which can be reduced following the initial Michael Scheme 2
SECORAPAMYCIN
III

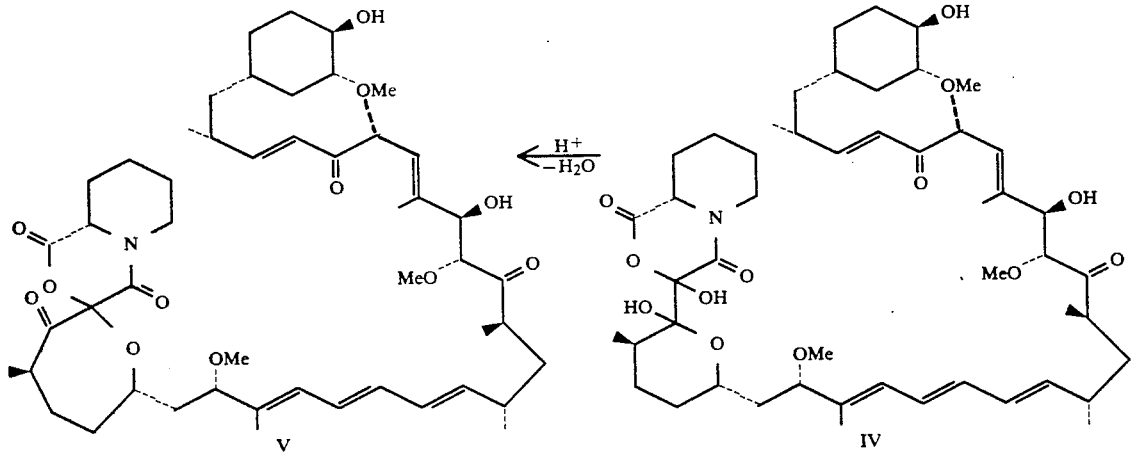

Treatment of secorapamycin (III) with reagents containing two nucleophilic centers, corresponding to X, as described above, provided the re-closed compounds of this invention. It is thought that the more nucleophilic addition of the first nucleophile. For X groups in which sulfur is the second nucleophile added, protection of the thiol group with a suitable protecting group, such as a silyl thioether, benzyl thioether, THP thioether, and the like provides proper regioselectivity.

The reagents corresponding to X used to prepare the compounds of the invention are commercially available or can be prepared by methods that are disclosed in the literature.

This invention also covers derivatives of compounds of structure I, in which the 31- and/or 42-hydroxyl groups have been functionalized with groups that have been previously used to derivatize rapamycin in these positions. These derivatives include acyl derivatives as described in U.S. Pat. No. 4,316,885, which is hereby incorporated by reference; fluorinated esters as described in U.S. Pat. No. 5,100,883, which is hereby incorporated by reference; amide esters as described in U.S. Pat. No. 5,118,677, which is hereby incorporated by reference; carbamates as described in U.S. Pat. No. 5,118,678, which is hereby incorporated by reference; aminoesters as described in U.S. Pat. No. 5,130,337, which is hereby incorporated by reference; ethers and acetals as described in U.S. Pat. No. 5,151,413, which is hereby incorporated by reference; aminoacyl esters as described in U.S. Pat. No. 4,650,803, which is hereby incorporated by reference; sulfonates and sulfamates as described in U.S. Pat. No. 5,117,203; silyl ethers as described in U.S. Pat. No. 5,120,842, which is hereby incorporated by reference; and sulfonylcarbamates as described in U.S. patent application Ser. No. 07/837,048. Methods for preparing the derivatives of the compounds structure I are described in the above patents. Additionally, this invention also covers inorganic esters of the 31- and/or 42-hydroxyl groups such as phosphate, nitrate, sulfinate, sulfonate esters, and the like, and organic esters of these inorganic acids. Based on this disclosure, other esters that can be formed at the 31- and/or 42-positions will be apparent to one skilled in the art. This invention also covers the use of the derivatives I in combination with other immunoregulatory agents, as described above, for use in inducing immunosuppression.

Immunosuppressive activity for a representative compound of this invention was evaluated in an in vitro standard pharmacological test procedure to measure lymphocyte proliferation (LAF) and in an in vivo standard pharmacological test procedure with evaluated the survival time of a pinch skin graft.

The comitogen-induced thymocyte proliferation procedure (LAF) was used as an in vivo measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An IC$_{50}$ was obtained for each test compound as well as for rapamycin. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{^3\text{H-control thymus cells} - {}^3\text{H-rapamycin-treated thymus cells}}{^3\text{H-control thymus cells} - {}^3\text{H-test compound-treated cells}}$$

A representative compound of this invention was also evaluated in an in vivo test procedure designed to determine the survival time of pinch skin graft from male BAB/c donors transplanted to male C$_3$H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound.

The following table summarizes the results of A representative compound of this invention in these two standard test procedures.

TABLE 1

| EVALUATION OF IMMUNOSUPPRESSIVE ACTIVITY | | | |
|---|---|---|---|
| | LAF | | Skin Graft |
| Compound | IC$_{50}$(nM) | ratio* | (days ± SD) |
| Example 2 | 5.1+ | 0.82 | 9.00 ± 0.63 |
| No Treatment | | | 7.00 ± 0.00 |
| Rapamycin | 4.2 | | 11.67 ± 0.63 |

*Calculation of the ratio was described supra.
+T-cell proliferation was inhibited by 96% at 0.1 μM and by 77% at 10 nM.

The results of these standard pharmacological test procedure demonstrate immunosuppressive activity both in vitro and in vivo for the compounds of this invention. Positive ratios in the LAF test procedures indicates suppression of T-cell proliferation, thereby demonstrating the immunosuppressive activity of the compounds of this invention. As a transplanted pinch skin grafts are typically rejected within 6–7 days without the use of an immunosuppressive agent, the increased survival time of the skin graft when treated with the compounds of this invention further demonstrates their utility as immunosuppressive agents.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because the compounds of this invention are structurally similar to rapamycin and have a similar activity profile to rapamycin, the compounds of this invention also are considered to have antitumor, antifungal activities, and antiproliferative activities. The compounds of this invention therefore also useful in treating solid tumors, fungal infections, and hyperproliferative vascular diseases such as restenosis and atherosclerosis.

Based on the results obtained in the standard pharmacological test procedures, the derivatives of formula I, as described above, are also useful for inducing immunosuppression, and in the treatment of transplantation rejection, hose vs. graft disease, autoimmune diseases, diseases of inflammation, solid tumors, fungal infections, and hyperproliferative vascular disorders.

As the compound of Example 2 [23,25-deepoxy-23,25-(2-aminoethanethio)rapamycin] was prepared via 25,26-dehydro-24,25-secorapamycin (Example 1), the compound of Example 1, or a base addition salt thereof, is therefore useful as an intermediate of the compound of Example 2.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parental administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parental administration, the carrier can also be an oily ester such as ethyl oleate and isopropyl myristate. Sterile liquid carriers are useful in sterile liquid form compositions for parental administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$g/kg-100 mg/kg, preferably between 0.001-25 mg/kg, and more preferably between 0.01-5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

25,26-Dehydro-24,25-secorapamycin

Method A

A stirred solution of rapamycin (1.8 g, 2 mmol) in 30 mL of absolute ethanol was treated with 2 mL of 1N NaOH and allowed to stand at room temperature for 1 hour. The solvent was evaporated under reduced pressure and the residue partitioned between ether and ethyl acetate. The aqueous phase was concentrated to dryness in vacuo to yield the sodium salt of the title compound as a light yellow solid (1.4 g, 77%). A portion (0.5 g) was further purified by MPLC (Lichroprep RP-8, 310×25 mm, acetonitrile/water (6:4), flow rate 20 mL/min) to provide 0.123 g of pure title compound as an off-white solid.

$^1$H NMR (400 MHz, DMSO-d$_6$): δ 1.552 (s, 3H, CH$_3$C=C), 1.695 (s, 3H, CH$_3$C=C), 2.969 (s, 3H, CH$_3$O), 3.148 (s, 3H, CH$_3$O), 3.29 (s, 3H, OCH$_3$), 6.11–6.14 (d, 1H, J=15 Hz, C=CH), 6.64 (m, 1H, C=CH), 10.0 (broad s, 1H, COOH).

$^{13}$C NMR (400 MHz, DMSO-d$_6$): .δ 212.8, 205.8, 199.7, 170.47, 166.64, 151.75, 138.59, 137.3, 132.67, 129.9, 128.6, 127.3, 126.3, 98.95.

MS (neg. ion FAB, m/z): 913 (M)$^-$, 590

Anal. Calc'd for C$_{51}$H$_{79}$NO$_{13}$+2.5H$_2$O: Theory: C, 63.96; H, 8.82; N, 1.46; Found: C, 63.85; H, 8.37; N, 1.19.

Method B

A mixture of 1.00 g of rapamycin (1.09 mmol), 0.146 g of 4-dimethylaminopyridine (1.1 eq) and 1 ml of dichloromethane was stirred overnight at 40° C. The reaction solution was cooled, diluted with ethyl acetate, and quickly washed with dilute acid. The organic solution was then washed with water and brine, dried over sodium sulfate, filtered and concentrated in vacuo to yield the crude title compound as a yellow solid. Purification of the crude product by flash column chromatography (Merck 60 silica gel, eluant: 15% isopropyl alcohol in methylene chloride) yielded the title compound that was identical to the material described in Method A.

EXAMPLE 2

23,25-Deepoxy-23,25-(2-aminoethanethio)-rapamycin 25,26-Dehydro-24,25-secorapamycin (1.2 g, 1.3 mmol) and 4-dimethylaminopyridine (0.176 g, 1.1 eq.) were dissolved in 5 ml of anhydrous methylene chloride under nitrogen at room temperature. 2-Mercaptoethylamine (0.203 g, 2 eq.) was added via syringe, the reaction was allowed to stir overnight, and worked up by adding ethyl acetate, dilute acid and brine. The ethyl acetate layer was separated and concentrated in vacuo. The crude product (1.0 g, 1.009 mmol) was dissolved in 50 mL of anhydrous methylene chloride at 0° C. under nitrogen and treated with 1-(3-dimethylaminopropyl)-3-ethylcarbodiimide.HCl (0.97 g, 5 eq.), 1-hydroxybenzotriazole hydrate (0.682 g, 5 eq.) and N-methylmorpholine (0.77 ml, 7 eq.). The reaction was then allowed to stir overnight while slowly reaching room temperature. Following work up with ethyl acetate, dilute acid and brine, the organic layer was dried over sodium sulfate, filtered and concentrated in vacuo to yield 1 gram of crude title compound. Further purification by flash column chromatography yielded 0.120 g of title compound as a mixture of diastereomers.

$^1$H NMR (DMSO-d$_6$) δ 8.0–7.2 (multiple absorptions, diastereomers/rotomers of amide NH), 6.55–6.33 (m, 2H), 6.30–6.0 (m, 3H), 5.7–5.4 (m, 2H), 5.4–5.17 (m, 2H), 3.33 (m, 3H methoxy), 3.25–3.11 (m, 3H methoxy), 3.0 (m, 3H methoxy)

$^{13}$C NMR (DMSO-d$_6$) all absorptions are multiple lines due to the presence of diastereomers) δ 214–211.5, 210–208.5, 200–199, 169.5–168.3, 167–166, 139.9–138.8, 138–135.5, 133.3–132.2, 130.2–129.4, 128–124.4, 99.5

MS (neg. ion FAB) m/z 972 [M]$^-$, 649, 321

Anal. Calculated for C$_{53}$H$_{84}$NO$_2$O$_{12}$S.2.5H$_2$O: Theory: C, 64.8; H, 8.7; N, 2.85; Found: C, 64.4; H, 8.8; N, 2.85.

What is claimed is:

1. A compound of the structure

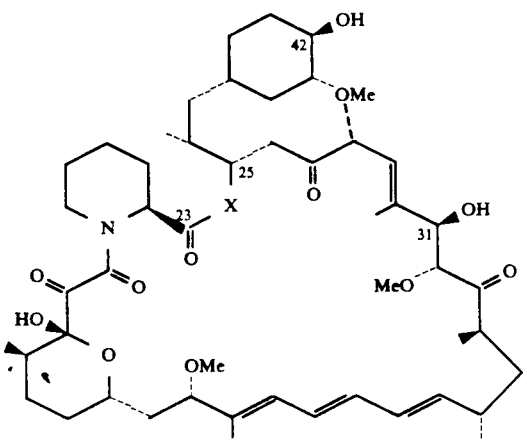

wherein
X is selected from the group consisting of —NR$^1$CR$^2$R$^3$(CR$^4$R$^5$)$_m$S—, —NR$^1$CR$^2$R$^3$(CR$^4$R$^5$)$_m$O—, —OCR$^2$R$^3$(CR$^4$R$^5$)$_m$O—, —NR$^1$CR$^2$R$^3$(CR$^4$R$^5$)$_p$—, —OCR$^2$R$^3$(CR$^4$R$^5$)$_p$—, —NR$^1$CR$^2$R$^3$(CR$^4$R$^5$)$_m$NR$^6$—, —OCR$^2$R$^3$(CR$^4$R$^5$)$_m$NR$^6$—, —SCR$^2$R$^3$(CR$^4$R$^5$)$_m$NR$^6$—, —SCR$^2$R$^3$(CR$^4$R$^5$)$_m$S—, —NOR$^1$—, and —NR$^1$—;

R$^1$, R$^2$, R$^3$, R$^4$, R$^5$, and R$^6$ are each, independently, hydrogen, alkyl of 1–6 carbon atoms, fluorine, trifluoromethyl, aryl, arylalkyl or 7–10 carbon atoms, or any pair taken together to form a 3–6 membered ring, wherein the aryl moiety of the aryl and arylalkyl groups is selected from the group consisting of phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, and benzodioxolyl which may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H;

m=1–6; and
p=0–6
or a pharmaceutically acceptable salt thereof.

2. The compound of claim 1 in which X is —NR$^1$CR$^2$CR$^2$R$^3$(CR$^4$R$^5$)$_m$S— or a pharmaceutically acceptable salt thereof.

3. The compound of claim 2 wherein R$^1$, R$^2$, R$^3$, R$^4$, and R$^5$ are each, independently, hydrogen or alkyl of 1–6 carbon atoms or a pharmaceutically acceptable salt thereof.

4. The compound of claim 1 which is 23,25-deepoxy-23,25-(2-aminoethanethio)rapamycin or a pharmaceutically acceptable salt thereof.

5. A method of inducing immunosuppression in a mammal in need thereof which comprises, administering to said mammal an immunosuppressive amount of a compound of the structure

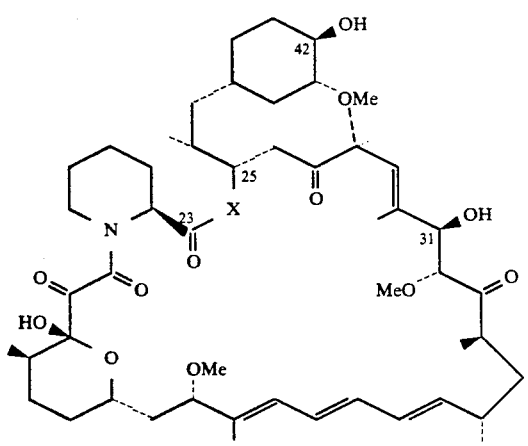

wherein

X is selected from the group consisting of
—$NR^1CR^2R^3(CR^4R^5)_mS$—,
—$NR^1CR^2R^3(CR^4R^5)_mO$—, —$OCR^2R^3(CR^4R^5)_mO$—, —$NR^1CR^2R^3(CR^4R^5)_p$—,
—$OCR^2R^3(CR^4R^5)_p$—, —$NR^1CR^2R^3(CR^4R^5)_mNR^6$—, —$OCR^2R^3(CR^4R^5)_mNR^6$—, —$SCR^2R^3(CR^4R^5)_mNR^6$—, —$SCR^2R^3(CR^4R^5)_mS$—, —$NOR^1$—, and —$NR^1$—;

$R^1$, $R^2$, $R^3$, $R^4$, $R^5$, and $R^6$ are each, independently, hydrogen, alkyl of 1-6 carbon atoms, fluorine, trifluoromethyl, aryl, arylalkyl or 7-10 carbon atoms, or any pair taken together to form a 3-6 membered ring, wherein the aryl moiety of the aryl and arylalkyl groups is selected from the group consisting of phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, and benzodioxolyl which may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$;

m=1-6; and
p=0-6 or a pharmaceutically acceptable salt thereof.

6. The method according to claim 5 wherein the induced immunosuppression is used to prevent or treat transplantation rejection or host versus graft disease.

7. The method according to claim 5 wherein the induced immunosuppression is used to treat autoimmune diseases, diseases of inflammation, or hyperproliferative vascular disorders.

8. A pharmaceutical composition which comprises an effective amount of a compound of the structure

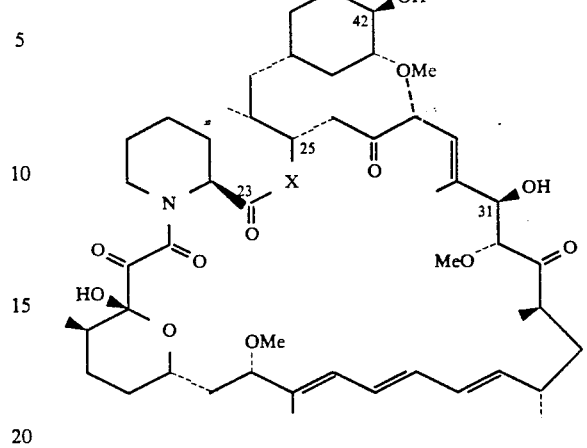

wherein

X is selected from the group consisting of
—$NR^1CR^2R^3(CR^4R^5)_mS$—,
—$NR^1CR^2R^3(CR^4R^5)_mO$—, —$OCR^2R^3(CR^4R^5)_mO$—, —$NR^1CR^2R^3(CR^4R^5)_p$—,
—$OCR^2R^3(CR^4R^5)_p$—, —$NR^1CR^2R^3(CR^4R^5)_mNR^6$—, —$OCR^2R^3(CR^4R^5)_mNR^6$—, —$SCR^2R^3(CR^4R^5)_mNR^6$—, —$SCR^2R^3(CR^4R^5)_mS$—, —$NOR^1$—, and —$NR^1$—;

$R^1$, $R^2$, $R^3$, $R^4$, $R^5$, and $R^6$ are each, independently, hydrogen, alkyl of 1-6 carbon atoms, fluorine, trifluoromethyl, aryl, arylalkyl or 7-10 carbon atoms, or any pair taken together to form a 3-6 membered ring, wherein the aryl moiety of the aryl and arylalkyl groups is selected from the group consisting of phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, and benzodioxolyl which may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —$SO_3H$, —$PO_3H$, and —$CO_2H$;

m=1-6; and
p=0-6 or a pharmaceutically acceptable salt thereof and a pharmaceutical carrier.

9. A method of inducing immunosuppression in a mammal which comprises administering to said mammal an immunosuppressive effective amount of a combustion of a compound of the structure

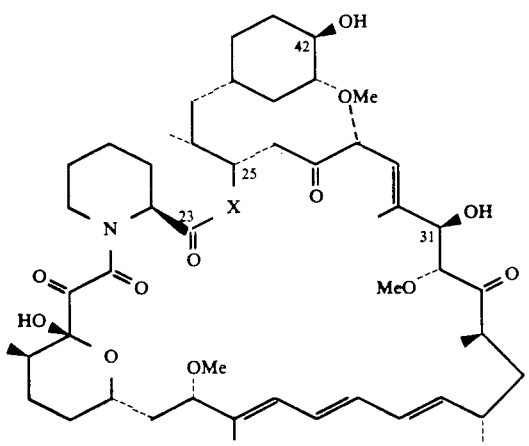
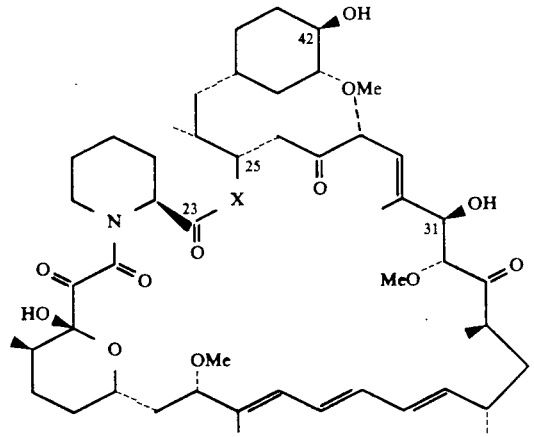

wherein

X is selected from the group consisting of
—NR¹CR²R³(CR⁴R⁵)$_m$S—,
—NR¹CR²R³(CR⁴R⁵)$_m$O—, —OCR²R³(CR⁴R⁵)$_m$O—, —NR¹CR²R³(CR⁴R⁵)$_p$—,
—OCR²R³(CR⁴R⁵)$_p$—, —NR¹CR²R³(CR⁴R⁵)$_m$NR⁶—, —OCR²R³(CR⁴R⁵)$_m$NR⁶—,
—SCR²R³(CR⁴R⁵)$_m$NR⁶—, —SCR²R³(CR⁴R⁵)$_m$S—, —NOR¹—, and —NR¹—;

R¹, R², R³, R⁴, R⁵, and R⁶ are each, independently, hydrogen, alkyl of 1-6 carbon atoms, fluorine, trifluoromethyl, aryl, arylalkyl or 7-10 carbon atoms, or any pair taken together to form a 3-6 membered ring, wherein the aryl moiety of the aryl and arylalkyl groups is selected from the group consisting of phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, and benzodioxolyl which may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;

m=1-6; and
p=0-6 or a pharmaceutically acceptable salt thereof and at least one other immunoregulatory agent.

10. The method according to claim 9 wherein the other immunoregulatory agent is selected from the group consisting of azathioprine, corticosteroids, such as prednisone and methylprednisone, cyclophosphamide, rapamycin, cyclosporin A, FK-506, OKT-3, and ATG.

11. A pharmaceutical composition which comprises an effective amount of a compound of the structure wherein X is selected from the group consisting of
—NR¹CR²R³(CR⁴R⁵)$_m$S—,
—NR¹CR²R³(CR⁴R⁵)$_m$O—, —OCR²R³(CR⁴R⁵)$_m$O—, —NR¹CR²R³(CR⁴R⁵)$_p$—,
—OCR²R³(CR⁴R⁵)$_p$—, —NR¹CR²R³(CR⁴R⁵)$_m$NR⁶—, —OCR²R³(CR⁴R⁵)$_m$NR⁶—,
—SCR²R³(CR⁴R⁵)$_m$NR⁶—, —SCR²R³(CR⁴R⁵)$_m$S—, —NOR¹—, and —NR¹—;

R¹, R², R³, R⁴, R⁵, and R⁶ are each, independently, hydrogen, alkyl of 1-6 carbon atoms, fluorine, trifluoromethyl, aryl, arylalkyl or 7-10 carbon atoms, or any pair taken together to form a 3-6 membered ring, wherein the aryl moiety of the aryl and arylalkyl groups is selected from the group consisting of phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, and benzodioxolyl which may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and —CO₂H;

m=1-6; and
p=0-6 or a pharmaceutically acceptable salt thereof; at least one other immunoregulatory agents; and a pharmaceutical carrier.

12. The composition according to claim 11 wherein the other immunoregulatory agent is selected from the group consisting of azathioprine, corticosteroids, such as prednisone and methylprednisone, cyclophosphamide, rapamycin, cyclosporin A, FK-506, OKT-3, and ATG.

13. A compound which is 25,26-dehydro-24,25-secorapamycin or a base addition salt thereof.

* * * * *